United States Patent [19]
Alberts et al.

[11] Patent Number: 5,851,537
[45] Date of Patent: Dec. 22, 1998

[54] TOPICAL APPLICATION OF α-DFMO FOR PREVENTING SKIN CANCER

[75] Inventors: David S. Alberts; Robert T. Dorr, both of Tucson, Ariz.

[73] Assignee: Cancer Technologies, Inc., Tucson, Ariz.

[21] Appl. No.: 792,619

[22] Filed: Jan. 31, 1997

Related U.S. Application Data

[60] Provisional application No. 60/010,613 Feb. 2, 1996.
[51] Int. Cl.$^6$ ........................... A61K 9/00; A61K 31/195
[52] U.S. Cl. ........................... 424/400; 514/561; 514/553
[58] Field of Search ........................... 424/400; 514/561, 514/553

[56] References Cited

U.S. PATENT DOCUMENTS

| | | |
|---|---|---|
| 4,433,051 | 2/1984 | Gilad et al. . |
| 4,818,770 | 4/1989 | Weinstein et al . . |
| 4,859,452 | 8/1989 | Ajani et al. . |
| 4,988,724 | 1/1991 | Ajani et al. . |
| 5,013,719 | 5/1991 | Bowlin . |
| 5,132,293 | 7/1992 | Shander ........................... 514/46 |
| 5,162,373 | 11/1992 | Ajani et al. . |
| 5,189,025 | 2/1993 | Ajani et al. . |
| 5,328,686 | 7/1994 | Shander ........................... 424/73 |
| 5,455,161 | 10/1995 | Assaraf et al. . |

OTHER PUBLICATIONS

McCullogh, et al., "Regulation of Epidermal Proliferation in Mouse Epidermis by Combination of Difluoromethyl Ornithine (DFMO) and Methylglyoxal Bis(guanylhydrazone)", 85: 516–521, 1985.

Gensler, "Prevention by α–difluoromethylornithine of skin carcinogenesis and immunosuppression induced by ultraviolet irradiation", J. Cancer Res Clin Oncol. 117: 345, 1991.

Alberts, et al., "Positive Randomized, Double Blinded, Placebo Controlled Study of Topical Difluoromethyl Orinithine (DFMO) in the Chemoprevention of Skin Cancer", Annual Meeting of the American Society of Clinical Oncology, vol. 15, May, 1996.

Takigawa et al., "Polyamine Biosynthesis and Skin Tumor Promotion: Inhibition of 12–0 Tetradecanoylphorbol–13–Acetate–Promoted Mouse Skin Tumor Formation by the Irreversible Inhibitor of Ornithine Decaboxylase α–Difluoromethylornithine", vol. 105, No. 3, p. 969, Apr. 14, 1982.

Meyskens, et al., "Phase II study of α–difluoromethylornithine (DFMO) for the treatment of metastatic lanoma", 4:257, 1986.

Weeks, et al., "α–Diluoromethylornithine, an irreversable inhibitor of ornithine decarboxylase, inhibits tumor promoter–induced polyamine accumulation and carcinogenesis in mouse skin", 79: 6028, Oct. 1982.

Grosshans, et al., "Les Polyamines Dans Le Psoriasis", 107:377, 1980.

Kishue J. of Nutritian, Growth & Cancer (1985) vol. 2 p. 91–99.

Takigawa Cancer Res. 43, 3732, 1983.

Kapyaho J. Invest. Dermatology 81, #2, p. 102, 1983.

*Primary Examiner*—Gollamudi S. Kishore
*Attorney, Agent, or Firm*—Cahill, Sutton & Thomas, P. L. C.

[57] ABSTRACT

A salve includes a water-miscible, hydrophilic cream vehicle, 1–22% by weight a-DFMO, and no absorption enhancer. The salve is preferably contained in an ointment tube permanently sealed at one end to preclude exposure to light and air. The salve is applied as a preventative in an appropriate amount twice daily to skin exposed to actinic radiation. An initial application of a salve including 10% by weight A-DFMO is preferred to minimize the risk of skin irritation without compromising the therapeutic value of the salve. The salve shows no systemic uptake, thereby eliminating systemic toxicities that result from other techniques for administering the drug.

5 Claims, No Drawings

TOPICAL APPLICATION OF α-DFMO FOR PREVENTING SKIN CANCER

CROSS-REFERENCE TO RELATED APPLICATION

This application is based upon Provisional Application Ser. No. 60/010,613 filed Feb. 2, 1996.

BACKGROUND OF THE INVENTION

This invention relates to the prevention of skin cancer and, in particular, to the topical application of alpha-DFMO for the prevention of skin cancer.

In the United States, more than 700,000 basal cell and squamous cell skin cancers are diagnosed annually and over 32,000 malignant melanomas are diagnosed annually, many in advanced stages. While the mortality rate for non-melanoma skin cancers is low, morbidity and medical costs of treatment are high. Furthermore, the incidence rates for all skin cancers are increasing. Most of these cancers are associated with sun exposure. Actinic keratoses may account for up to sixty percent of all squamous skin cell cancers and are commonly found in sun-exposed skin sites of light-skinned populations.

A variety of local treatments are used to treat actinic keratoses and thereby prevent malignant transformation to squamous cell carcinomas. These include the application of topical five percent fluorouracil cream and, more commonly, cryosurgical application of liquid nitrogen. Both procedures cause inflammation, erythema and superficial ulceration. Except for avoiding sunlight exposure, there are no known preventive measures which can lower the incidence of actinic keratosis development or their subsequent transformation to squamous cell cancer.

Studies have shown that numerous highly proliferative types of cancer are associated with increased levels of the polyamines putrescine, spermidine, and spermine in blood and urine. Further studies have shown that this is related to increased polyamine synthesis by the rate-limiting enzyme, ornithine decarboxylase (ODC). Similar effects have been observed in human psoriatic or cancerous skin. Keratinocytes are known to experience an increase in ODC activity when exposed in vitro to ultraviolet B (UVB) radiation. Increased ODC activity has also been reported in the epidermis following UV light exposure in vivo. Polyamine depletion has been suggested as one possible pharmacologic means of reducing the incidence or severity of pre-cancerous proliferative diseases such as actinic keratosis.

Eflornithine or alpha-difluoromethylornithine (α-DFMO) is a structural analog of the amino acid L-ornithine. Biochemically, (α-DFMO acts as a "suicide" substrate inhibitor of ornithine decarboxylase, the rate-limiting enzyme in polyamine synthesis. α-DFMO blocks the conversion of ornithine to putrescine and thereby lowers polyamine levels. Polyamines are known to bind to the outer helix of DNA and to control the rate of DNA synthesis by modulating the rate of movement of a DNA replication fork. Polyamines are also required to maintain the integrity of microfilaments and microtubules and to modulate the translation of specific ribosomal codons. The inhibition of ornithine decarboxylase by eflornithine is time and concentration dependent but is irreversible.

Another polyamine synthesis inhibitor, mitoguazone (MGBG) has also been shown to decrease the proliferation of cultured normal keratinocytes in vitro. When administered topically or intralesionally, MGBG produces therapeutic effects in psoriasis and in various cutaneous malignancies. However, topical MGBG is highly irritating, which mitigates against its use as a chronic topical chemopreventive agent for skin cancer.

It is known in the art that a topically applied, five percent solution of αDFMO blocks the synthesis of DNA in mouse epidermis in vitro: putrescine levels were decreased to twenty-five percent of control but spermine and spermidine levels were not affected. The application of a ten percent αDFMO cream in ten patients suffering from psoriasis was shown to reduce cutaneous spermine levels by sixty-six percent, with a marginal improvement in psoriatic lesions. The cream included an absorption enhancer, causing systemic uptake in the patients.

Orally administered α-DFMO has been shown to reduce skin cancer incidence and immunosuppression caused by UVB radiation in mice. A 1% α-DFMO solution in drinking water reduced UVB induced skin cancer incidence from 38% to 9%. In addition, the oral α-DFMO regimen also prevented UVB-induced immunosuppression. However, the 1% drinking water solution used in this prior study also caused sound-induced hyperactivity and a 16% body weight loss in treated mice.

Similarly, oral α-DFMO in humans is associated with ototoxicity which limits recommended doses for chemoprevention to a single 0.5 $g/m^2$ dose given daily. This clinical dose produced peak α-DFMO plasma concentrations of 47.1 $\mu$m, a terminal phase half life of 3.5 hours, and a plasma concentration×time product of 311 $\mu$m×hr in human subjects. Five of seven subjects receiving this oral dose had a $\geq 50\%$ reduction in skin ODC levels measured 6 hours after dosing. Skin levels of α-DFMO were not reported, but the ODC inhibition results suggest that the drug does distribute into the skin after oral dosing. The dose limiting toxic effect of α-DFMO is thrombocytopenia (abnormally few platelets in the blood), which occurs in about fifty percent of patients, leukopenia (abnormally few leukocytes), or anemia. A second major toxic effect of α-DFMO is nausea and vomiting, which occurs in up to ninety percent of the patients.

In view of the foregoing, it is therefore an object of the invention to provide a topical chemopreventive for skin cancer having minimal or no significant systemic uptake in human beings.

A further object of the invention is to provide a salve that can be used as a chronic topical chemopreventive agent for skin cancer.

A further object of the invention is to provide a topical salve that contains a chemopreventive agent for skin cancer but does not irritate the skin.

Another object of the invention is to provide a chemopreventive agent for skin cancer having minimal side effects.

SUMMARY OF THE INVENTION

The foregoing objects are achieved in this invention in which a salve includes a water-miscible, hydrophilic cream vehicle, 1–22% by weight α-DFMO, and no absorption enhancer. The salve is preferably contained in an ointment tube permanently sealed at one end to preclude exposure to light and air. The salve is applied as a preventative in an appropriate amount twice daily to skin exposed to actinic radiation. An initial application of a salve including 10% by weight α-DFMO is preferred to minimize the risk of skin irritation without compromising the therapeutic value of the salve. The salve shows no systemic uptake, thereby eliminating systemic toxicities that result from other techniques for administering the drug.

DETAILED DESCRIPTION OF THE INVENTION

The polyamine synthesis inhibitor eflornithine was studied for stability, tolerance, and penetration through mouse skin and human (cadaver) skin in the following manner.

Materials and Methods

α-DFMO was supplied as a white powder of the monohydrate, monochloride (MW=236.65) from Marrion-Merrell Dow Pharmaceutical Company (Lot No. 71,782A, Kansas City, Mo.). The drug was weighed and mixed by blender into a hydrophilic cream base (Vanicream®, Lot No. 637, Pharmaceutical Specialties, Inc., Rochester, Minn.). The final concentration was 1%, 5% or 10% (w/w) for toxicity studies and 10% (w/w) for all of the in vitro transdermal α-DFMO penetration studies. Vanicream's was chosen as the final vehicle for α-DFMO due to its non-greasy (water-miscible) composition which does not contain perfumes, dyes, lanolin, formaldehyde or parabens that might produce extraneous pharmacologic effects in mouse or human skin.

Once mixed, the cream was transferred to polyethylene-lined, 30 gram metal ointment tubes which were then crimp-sealed to preclude exposure to light and air. Some early α-DFMO uptake experiments were also performed using α-DFMO mixed at a 10% w/w concentration in hydrophilic ointment U.S.P. (Lot No. 0210, E. Fougera and Company, Melville, N.Y.).

Chemicals used in the high performance liquid chromatography (HPLC) assay for Lot No. 71,782A-DFMO were all of reagent or HPLC grade.

Animals:

Adult female BALB/c mice, 25–31 gm. weight, were obtained from Jackson Laboratories, Bar Harbor, Me. For toxicology tests, the mice were housed 5/cage and received standard lab chow and tap water ad libitum. A 12-hour light/dark cycle in a humidified atmosphere was utilized. Toxicology Study A cohort of 20 mice were de-haired over a 2 $cm^2$ dorsal area using the topical depilatory agent, Nair® Lotion (Carter Wallace, Inc., New York, N.Y.). Twenty-four hours later, the mice began treatment with topical α-DFMO cream: 50 mg of 1%, 5% or 10% α-DFMO daily, Monday–Friday, for four consecutive weeks (twenty applications). The daily dose was delivered by a positive displacement pipette (Micro-Man®, Gilson Scientific, Woburn, Mass.). This corresponds to daily doses of 0.5 mg, 2.5 mg, or 5 mg α-DFMO/day and total doses of 10, 50, and 100 mg for the four weeks for the 1%, 5%, and 10% formulations, respectively.

Using the murine total body surface area conversion nomogram of Freireich et al., the daily doses for the 3 cream concentrations of 1%, 5% and 10% were 71.4 $mg/m^2$, 357 $mg/m^2$, 714 $mg/m^2$. For the total four week period, the cumulative doses were 1.43 $g/m^2$, 7.14 $g/m^2$ and 14.28 $g/m^2$. A total of 20 mice were randomized to 4 treatment groups: 1) Vanicream® control; 2) 1% α-DFMO; 3) 5% α-DFMO; and 4) 10% α-DFMO. The skin application sites were observed daily for evidence of any local toxicity (erythema, induration or ulceration) and the animals were weighed weekly. At the end of the four week treatment period, the mice were sacrificed by rapid cervical dislocation and blood samples were obtained for quantifying renal function (BUN, creatinine), hepatic function (SGOT-SGPT, bilirubin), electrolytes ($Na^+ K^+ Cl^-$, $HCO_3^-$), hematologic indices (WBC with differential, RBC, platelets) and glucose (Animal Diagnostic Laboratories, Tucson, Ariz.).

α-DFMO Analysis

α-DFMO Analysis was evaluated using pre-column derivation of α-DFMO with the reagent, 6-aminoquinolyl-Nhydroxysuccinimidyl carbamate (Waters Acc Q-Fluor™, Reagent Kit, Lot No. KSBM1042, Millipore, Inc., Bedford, Mass.) [21]. The reverse phase (C-18 column, Alitech Associates, 150 mm×4.6 mm, 5 gm particle size) assay was performed with a 30 minute gradient elution using two mobile phases (A and B) containing aqueous buffer and acetonitrile, respectively. Mobile phase A contained 100 mM sodium acetate, 15 mM triethylamine, and 2.7 μm sodium EDTA dissolved in water at pH 5.0. Mobile phase B was acetonitrile UV® (Burdick & Jackson, Muskegon, Mich.). The starting proportion, A:B, was 92:8, at 18 min. it was 80:20; at 19–21 min. 40:60; and at 22–30 min. 92:8 [21]. The mobile phase was pumped at 1.2 mL/min. using a Perkin Elmer Biocompatible Binary Pump, a Hitachi AS-2000 Autosampler and a Hewlett Packard Series 1050 Solvent Programmer. The retention time of derivatized α-DFMO is 7.9 minutes compared to 15.0 minutes for the internal standard gamma-aminobutyric acid (GABA). The detection limit using fluorescence (244 nm excitation, 380 nm emission) was 90 fmol of α-DFMO using a BAS Model FL-45 detector.

For the stability assays, the 10% cream formulation was stored at 4° C. for up to 6 months and 10 μL aliquots were removed weekly and analyzed by HPLC after extraction using 1 mL distilled water.

α-DFMO Skin Penetration

α-DFMO skin penetration was evaluated in vitro using full thickness de-haired mouse skin from previously untreated BALB/c mice or human abdominal skin obtained freshly from cadavers. Percutaneous penetration of αα-DFMO was measured in glass diffusion cells (LG-1084, Skin Permeation Systems, Inc., Berkeley, Calif.) at 37° C. which expose a 1.0 $cm^2$ skin sample to 3.5 mL of collection fluid (Bacteriostatic 0.9% Sodium Chloride for Injection, U.S.P., Abbott Laboratories, North Chicago, Ill.). This methodology has been described previously in detail in the literature. For these experiments, 200 μL of 10% w/w α-DFMO cream in either hydrophilic ointment or Vanicream® was applied to the skin and 10 samples of collection fluid were obtained thereafter at 1, 2, 4, 6, 8, 12 and 24 hours for HPLC analysis of α-DFMO content.

Extraction of α-DFMO from skin samples was performed on 5 mg samples. These were minced by scissors and then sonicated for 30 seconds in 100 μL of (0.4 m) $HClO_4$ containing 10 mM internal standard GABA. To this mixture, 100 μL of water was added and the contents were then centrifuged at 10,000×G for 3 min. A 10 μL aliquot of supernatant was added to 40 μL of sodium tetraborate solution (pH 9.3) and mixed with 10 of the derivatizing agent 6-aminoquinolyi-N-hydroxysuccinimidyl carbamate. This mixture was then heated for 10 min. at 50° C. and a 20 μL aliquot was injected into the HPLC.

Toxicity

The α-DFMO treated mice survived through the study period without drug related alterations in weight gain which averaged 0.132 (±157) week. Blood analyses at the end of the 4 week dosing period revealed no alterations in serum enzymes, electrolytes or hematologic parameters, when compared to the Vanicream's-treated control group. Hair regrowth also proceeded normally in each group and there was no evidence of local skin irritation in any group.

α-DFMO Assays and Stability

The HPLC assay efficiently separated α-DFMO from the internal standard, α-aminobutyric acid (GABA). The retention time of derivatized α-DFMO was 9.8 minutes compared to 12.9 minutes for derivatized GABA. The sensitivity of the assay was 0.02 mM for a 20 μL injection with a day to day coefficient of variation of 6.1%. Using this assay, α-DFMO in Vanicream® was chemically stable for 6 months when stored at 4° C. in sealed metal tubes. There was <1% loss of α-DFMO noted at the six month time point.

α-DFMO Skin Penetration

In mouse skin at 37° C., α-DFMO transdermal penetration was maximal after 24 hours and the mean percent uptake was 61.53% of the applied dose. The degree of penetration was much lower in human skin, amounting to only 0.7% of the applied concentration after 24 hours of incubation at 37° C. The calculated penetration rate in mouse skin was 3.6 [μg/cm$^2$/hour for the 10% α-DFMO formulation in Vanicream ®. In hydrophilic ointment U.S.P., the rate of penetration of α-DFMO in mouse skin was similar to that in Vanicream ® although maximal penetration occurred earlier, after only 12 hours of incubation at 37° C. (data not shown).

The mouse and human skin samples treated with 10% α-DFMO in Vanicream® were also analyzed for α-DFMO content after 1, 2, 4, 6, 24 and 41 hours of incubation at 37° C. The results show that uptake into mouse skin (mean DFMO skin weights of 62.3±11.8 mg/cm$^2$ peaked at 7.25 mg/gm skin after only 4 hours of incubation. In contrast, α-DFMO uptake into human skin was much slower with a peak uptake of 0.323 mg/gm after 24 hours of contact with the 10% cream. No transdermal human skin penetration was apparent until after 20 hours of exposure to α-DFMO cream at 37° C. The cumulative uptake of α-DFMO in human skin represents only 5% of the uptake achieved in mouse skin. This degree of uptake produced a human skin tissue concentration of 1.36 mM, assuming that 1 g of skin tissue approximates 1 mL of fluid volume. Thus, skin uptake and transdermal penetration of α-DFMO are significantly lower in human skin compared to mouse skin. Nonetheless, substantial intradermal levels of α-DFMO are achieved in the skin of both species.

These studies have shown that α-DFMO blended into an aqueous-miscible cream base, is chemically stable for at least 6 months at 4° C. This topical formulation is nontoxic in mice and facilitates significant α-DFMO uptake into and penetration through mouse skin. Uptake is substantially lower in human cadaver skin. This is compatible with prior studies showing a greater flux of marker compounds through mouse skin compared to human skin. The degree of transdermal penetration of 10% α-DFMO in the Vanicream® formulation in mice was substantially less than that reported for 5% α-DFMO in an azone-containing formulation.

A randomized, placebo controlled phase IIb cancer control study using a topical hydrophilic ointment formulation with or without 10% (w/w) α-DFMO. Forty-eight participants with severe actinic keratoses (AKs) on their forearms (i.e. at least ten well circumscribed lesions nonlateral, sun-exposed surfaces) completed a one month run-in on placebo ointment applied twice daily to the affected areas. Prior to randomization of each participant's left or right forearm to receive placebo or α-DFMO, all lateral forearm AKs were circled, counted, photographed, and skin biopsies were obtained for DFMO and polyamine levels. After six months of treatment, all measurements were repeated. Four participants experienced skin rash in the area of DFMO application, one moderately severe. α-DFMO was not detected in blood and there were no systemic toxicities. None of a subsample of seventeen placebo forearms had measurable concentrations of DFMO, whereas thirteen of the corresponding α-DFMO treated forearms had high DFMO skin levels. As compared to placebo, the six month α-DFMO treatment caused a 21% reduction in the number of AKs and a 21% suppression of total polyamines. The study was described at the thirty-second annual meeting of the American Society of Clinical Oncology on May 18–21, 1996.

The invention thus provides a topical chemopreventive for skin cancer having minimal or no significant systemic uptake in human beings that irritates the skin in relatively few patients. The salve can be used as a chronic topical chemopreventive agent for skin cancer and has minimal side effects.

Having thus described the invention, it will be apparent to those of skill in the art that modifications can be made within the scope of the invention. For example, the dosage can be increased to about 22% α-DFMO, the solubility limit in the particular vehicle used. Any water miscible vehicle can be used provided that the vehicle does not contain perfumes, dyes, lanolin, formaldehyde or parabens that might produce extraneous pharmacologic effects in human skin. Also, the vehicle cannot contain absorption enhancers.

What is claimed as the invention is:

1. A method for the reduction of actinic keratoses (Aks) in human skin, said method including the steps of:

providing a salve containing between 1–22 % by weight α-DFMO; and applying an appropriate amount of the salve to skin containing actinic keratoses.

2. The method as set forth in claim 1, wherein said applying step is performed twice daily.

3. The method as set forth in claim 1, wherein said salve does not include any absorption enhancer.

4. The method as set forth in claim 1, wherein said salve includes a water-miscible hydrophilic cream base.

5. The method as set forth in claim 1, wherein said salve includes approximately 10% by weight α-DFMO.

* * * * *